United States Patent [19]

Ishii et al.

[11] 4,200,694
[45] Apr. 29, 1980

[54] NOVEL PECTIN ESTERASE, PROCESS FOR ITS PRODUCTION, AND PROCESS FOR PRODUCING DEMETHOXYLATED PECTIN BY THE USE OF SAID PECTIN ESTERASE

[75] Inventors: Shigetaka Ishii, Noda; Keiichi Kiho, Toyohashi; Shinichi Sugiyama; Hiroshi Sugimoto, both of Noda, all of Japan

[73] Assignee: Kikkoman Shoyu Co., Ltd., Noda, Japan

[21] Appl. No.: 945,882

[22] Filed: Sep. 26, 1978

[30] Foreign Application Priority Data

Oct. 8, 1977 [JP] Japan ................................. 52-120504
Oct. 12, 1977 [JP] Japan ................................. 52-121398

[51] Int. Cl.$^2$ ........................ C12D 13/04; A23L 1/04
[52] U.S. Cl. .................................. 435/101; 435/197; 435/275; 426/50; 435/913; 435/917; 435/935; 435/929; 435/911; 426/577; 536/2
[58] Field of Search ................. 195/62, 65, 7; 426/50, 426/577

[56] References Cited

U.S. PATENT DOCUMENTS

| | | | |
|---|---|---|---|
| 2,801,178 | 7/1957 | Leo et al. | ................................. 426/50 |
| 3,622,559 | 11/1971 | Wiles . | |

OTHER PUBLICATIONS

Advances in Carbohydrate Chemistry and Biochemistry, vol. 33, (1976), pp. 323, 329–337.
Journal of American Chemical Society, vol. 68 (Feb. 1946), pp. 287–293.
Journal of Phys. and Colloid Chem. vol. 51 (1947), pp. 117–133.
Food Technology, vol. 3 (Mar. 1949), pp. 90–93.

*Primary Examiner*—Lionel M. Shapiro

[57] ABSTRACT

A novel pectin esterase which randomly hydrolyzes the methyl ester bond of pectin can be obtained by cultivating, on a medium, a mold strain belonging to Genus Aspergillus, Genus Penicillium, Genus Fusarium or Genus Sclerotinia and having an ability to produce said novel pectin esterase. A demethoxylated pectin having a uniform methoxyl group content can be obtained by adding said novel pectin esterase to pectin. The demethoxylated pectin thus obtained can be utilized as gelling agent, emulsifier or thickener for food processing.

11 Claims, 3 Drawing Figures

FIG. 2

NOVEL PECTIN ESTERASE, PROCESS FOR ITS PRODUCTION, AND PROCESS FOR PRODUCING DEMETHOXYLATED PECTIN BY THE USE OF SAID PECTIN ESTERASE

This invention relates to a novel pectin esterase obtainable by the use of a mold belonging to Genus Aspergillus, Genus Penicillium, Genus Fusarium or Genus Sclerotinia, as well as to a process for its production. This invention also relates to an enzymatic process for producing a demethoxylated pectin having a uniform methoxyl group content by the use of said pectin esterase.

The pectin esterase obtainable by the process of this invention is a novel enzyme which is different from the hitherto known pectin esterases in substrate specificity especially, in random manner of hydrolysis of the methyl ester bond of pectin.

Pectin is a polysaccharide found in higher plants such as fruits, vegetables, etc. It is a water-soluble, colorless, tasteless, odorless, amorphous substance of which main structure is a long chain sequence composed of $\alpha$-1,4 linkage of D-galacturonic acid units and of which carboxyl groups are partially esterified to form methoxyl group ($-OCH_3$). A solution of pectin is viscous and it forms a gel when heated together with both sugar and acid under appropriate conditions and then cooled, so that it has long been utilized in the manufacture of foods as gelling agent for jelly, jam, marmalade or the like, and also as an emulsifier or a thickener.

If the carboxyl groups of pectin molecule is fully esterified to form methyl ester, the pectin has a methoxyl group content of 16.32%. From the viewpoint of the mechanism of gelation, pectin is classified into two types according to the content of methoxyl group. That is, pectins containing 7% or more methoxyl group are called "high-methoxyl pectin", while those containing less than 7% of methoxyl group are called "low-methoxyl pectin". A gel of high-methoxyl pectin is hydrogen bonding type, while a gel of low-methoxyl pectin is ionic bonding type.

The pectin utilized from the old time is usually high-methoxyl pectin. Its gelation requires to use both sugars in an amount of 60% or more and an appropriate amount of acids. Moreover, the condition of gelation must be controlled strictly, therefore, procedure of gelation is very sophisticated. On the contrary, the gelation of low-methoxyl pectin does not always require to add sugar and acid, but the gelation is easily carried out in the presence of just metal ions such as calcium ion. This simplifies the procedure and makes it possible to produce a jelly or a jam of low sugar content. In addition, the use of this type of pectin is being expanded not only as gelling agent but also as film-forming agent for yogurt, mayonnaise, etc.

If the natural high-methoxyl pectin obtainable from plant origins such as fruits can be demethoxylated by some means into a low-methoxyl pectin, the procedure of gelation will be simplified and the application field will be expanded. Based on this idea, a variety of processes have hitherto been proposed for its demethoxylation. The processes hitherto proposed include, for examples, (1) the process by the use of acid, (2) the process by the use of alkali, (3) the process by the use of enzyme, and (4) the process by the use of ammonia.

However, these processes are disadvantageous in the following points. Thus, process (1) is disadvantageous in that the demethoxylation reaction proceeds too slowly and it is always accompanied with degradation of pectin to some extent, which reduces the gel strength greatly. In addition, this process requires acid-tolerable apparatuses. Process (2) in which alkyli such as sodium hydroxide is used gives a much higher reaction rate of demethoxylation as compared with the use of acid. However, this character of process (2) means that degradation of pectin itself also occcurs simultaneously. Process (3) in which demethoxylation is carried out by the aid of pectin esterase, an enzyme hydrolyzing the methoxyl group of pectin, appears to be ideal in that demethoxylation can be preformed rapidly under mild conditions without any degradation of pectin itself. However, as a matter of fact this process has a significant faulty that the low-methoxyl pectin obtained by this process is always quite poor in an ability of gel formation.

Thus, it is a current trend to carry out the demethoxylation of pectin by the ammonia process (4). This process, however, is still disadvantageous in that degradation of pectin unavoidably occurs to some extent, that the low-methoxyl pectin produced by this process contains a considerable quantity of amide group newly formed, and that this process consumes a large quantity of ammonia of which desposal sets us another problem.

Nevertheless, the present inventors have considered that an enzymatic process would be fundamentally the best way to produce a low-methoxyl pectin having an ability to form strong gel under mild conditions without degradation of pectin, and conducted intensive studies on this basis.

The enzyme hitherto employed for hydrolyzing the methyl ester bond of pectin, namely pectin esterase (hereinafter referred to as PE), has an action specificity that the enzyme first acts upon a certain specific positions of methoxyl group in the pectin molecule and then successively propagates its action, as mentioned in the Hills' paper [Food Technol., 3, 90 (1949)]. Accordingly, when PE acts upon a high-methoxyl pectin, a certain molecule may be demethoxylated to a considerable extent to the level of low-methoxyl pectin but another pectin molecule may be entirely or almost completely intact from demothoxylation. In other words, the degree of demethoxylation is not equal among pectin molecules. For example, when PE acts on a high-methoxyl pectin having a methoxyl content of 10% in order to produce a low-methoxyl pectin having a methoxyl content of 5%, in an extreme case the product may be a 1:1 mixture of molecules containing 0% methoxyl group and molecules containing 10% methoxyl group which gives a methoxyl group content of 5% in average. Such great variety in methoxyl group content among molecules is considered to be the main cause for the low gel forming ability of low-methoxyl pectin prepared by hitherto reported PE.

Accordingly, the present inventors considered that, if one used a PE which randomly acted on methoxyl group of pectin as well as acid, alkali or ammonia, which had such an action specificity as to hydrolyzes the methyl ester bond of the pectin molecules in random manner, and which did not decompose the $\alpha$-1,4 bond of D-galacturonic acid, there would be obtained a pectin having a uniform and appropriately decreased methoxyl group content, namely a low-methoxyl pectin having an ability to form a strong gel. Based on this consideration, the inventors have searched for a new microbial strain having an ability to produce a novel PE having the above-mentioned action specificity. As the result, it has been found that a novel PE which randomly hydrolyzes the methyl ester bond of pectin could be obtained by cultivating a mold strain belonging to Genus Aspergillus, Genus Penicillium, Genus Fusarium or Genus Sclerotinia on the conventional solid or liquid medium, and that when this novel PE was added to pectin there could be obtained a demethoxylated pectin having an ability to form strong gel and a uniform methoxyl group content by an enzymatic process. Based on these findings, this invention has been accomplished.

Those are objects of this invention to provide a novel pectin esterase and a process for its production.

It is another object of this invention to provide a enzymatic process for the production of demethoxylated pectin having a uniform methoxyl group content which comprises adding said novel pectin esterase to pectin.

The objects and advantages of this invention will be demonstrated more clearly from the following descriptions.

According to this invention, there are provided a novel pectin esterase and a production process thereof, characterized by cultivating a mold strain belonging to Genus Aspergillus, Genus Penicillium, Genus Fusarium or Genus Sclerotinia and having an ability to produce a novel pectin esterase which randomly hydrolyzes the methyl ester bond of pectin, followed by collecting said novel pectin esterase from the culture. According to this invention, there is also provided an enzymatic process for producing demethoxylated pectin characterized by adding said novel pectin esterase to pectin, randomly hydrolyzing the methyl ester bond of pectin therewith, and thereby obtaining a demethoxylated pectin having a uniform methoxyl group content.

Among the accompanying drawings.

First of all, the enzymatic and physico-chemical properties of the novel PE produced according to the process of this invention will be mentioned.

(1) Action and substrate specificity:

This enzyme acts upon the methyl ester bond of pectin and hydrolyzes it in random manner. Its action is specific to the methyl ester bond of pectin and inert to ethyl ester, propyl ester and ethylene glycol ester bonds.

(2) Optimum pH for its action and stable pH range:

Optimum pH for its action is about 4.5 and stable pH range is 3 to 6.

(3) Measurement of activity:

The activity of the novel PE can be measured in the following way. Thus, 1 ml of enzyme solution dissolved in 0.05 M acetate buffer (pH 4.5) is mixed with 1 ml of 1% solution of commercial pectin, Pectin N.F. (Trademark Sunkist Growers Inc., U.S.A.) dissolved in the same buffer solution as mentioned above, and incubated at 30° C. for 10 minutes, after which the reaction is stopped by pouring the reaction mixture into 2 N $H_2SO_4$. The reaction mixture contains methanol formed during the demethoxylation of pectin. The methanol is oxidized with potassium permanganate, reacted with pentan-2,4-dione and ammonia and then estimated absorbancy at 412 nm. An enzymic activity showing an absorbancy of 0.84 per reaction time of one minute is regarded as one unit.

(4) Range of optimum temperature for its action:

The optimum temperature for its action is in the range of 25° to 50° C., in particlar 40° to 45° C.

(5) Inactivating pH and temperature:

The enzyme completely loses its activity upon treatment at 60° C. for 10 minutes. It also loses its activity below pH 2 or above pH 8.

(6) Inhibition, activation and stabilization:

It is inhibited by $Hg^{++}$, $Cu^{++}$ and $Ag^+$. No particular activator and stabilizer is found.

(7) Molecular weight:

This enzyme has a molecular weight of 35,000 in 0.1 M ammonium acetate buffer solution at 4° C. and pH 5.0, as measured by means of gel-filtration method with Sephadex G-100 (Tradename, manufactured by Pharmacia Co., Sweden) according to the method of Andrews [P. Andrews: Biochem. J., 96, 595 (1965)].

(8) It is an acidic protein having an isoelectric point of PI 4.1.

In Table 1, the enzyme of this invention mentioned above is compared with the hitherto known PE.

Table 1

| Substrate specificity | PE of this invention It is specific to the methyl ester bond of pectin and randomyl hydrolyzes the methyl ester bond. | PE originated from tomato*1 Its hydrolysis of pectin methyl ester starts at a certain specific position and propagates successively. | PE originated from Clostridium multifermentance*2 Its hydrolysis starts at the reducing end group of pectin molecule. |
|---|---|---|---|
| $K_m$ value | $3.2 \times 10^{-3}$ M | $4 \times 10^{-3}$ M | $2.5 \times 10^{-3}$ M |
| Molecular weight | 35,000 | — | 400,000 |
| Optimum pH | 4.5 | 6–9 | 9.0 |
| Optimum action temperature | 40°–45° C. | — | 25°–35° C. |
| Activator(s) | Nil | 0.0 M $CaCl_2$ 0.05 M NaCl | 0.05 M NaCl |
| Inactivation temperature | 60° C. for 10 minutes | — | 38° C. for 30 minutes |
| Inhibitor(s) | $Hg^{++}$, $Cu^{++}$, $Ag^+$ | Polygalacturonic acid | — |

*1: The enzyme mentioned in Biochem, 7, 4005–4010 (1968)
*2: The enzyme mentioned in Bacteriol, 102, 72–78 (1970) and 103, 595–600 (1970).

As described above, the novel enzyme obtainable according to this invention is different from any known PE in enzymatic and physico-chemical properties, so that the enzyme can be concluded as a novel enzyme.

The production process of the novel enzyme of this invention will be mentioned below more concretely.

The microorganism used in this invention is a mold strain which belongs to Genus Aspergillus, Genus Penicillium, Genus Fusarium or Genus Sclerotinia and has an ability to produce the novel PE. Concrete examples of the mold strain belonging to Genus Aspergillus include *Aspergillus japonicus* No. 1744 ATCC 20236, and *Aspergillus niger* ATCC 1015; concrete example of the mold strain belonging to Genus Penicillium includes *Penicillium chrysogenum* ATCC 10107; concrete example of the mold strain belonging to Genus Fusarium includes *Fusarium oxysporum* ATCC 15653; and concrete example of the mold strain belonging to Genus Sclerotinia include *Sclerotinia archidis* IFO 5291, *Sclerotinia libertiana* ATCC 20025 and the like. All these strains can be obtained from the organizations in which the strains have been deposited.

The mold strains usable in this invention are, however, not limited to above, and all the molds belonging to Genus Aspergillus, Genus Penicillium, Genus Fusarium or Genus Sclerotinia and simulataneously having an ability to produce the novel PE can be used in this invention.

The mold strains having an ability to produce an enzyme which randomly hydrolyzes the methyl ester bond of pectin can be cultivated on either solid or liquid medium in the conventional manner used for the cultivation of molds.

As nutrient for the medium, a wide variety of substances conventionally employed for the cultivation of microogranisms may be used.

As the carbon source, any carbon compound assimilable or any substances containing said carbon compound may be used. Examples of said carbon source include one or more members selected from wheat, wheat bran, glucose, sucrose, starch, maltose, dextrin, glycerol and the like. As the nitrogen source, any nitrogen compound utilizable or any substances containing said nitrogen compound may be used. Examples of said nitrogen source include one or more members selected from soybean meal, soybean flour, defatted soybean flour, wheat gluten, peptone, meat extracts, milk casein, corn steep liquor, ammonium sulfate and ammonium chloride. Also, inorganic salts such as those of phosphorus, potassium, magnesium, calcium and the like may be used appropriately. Furthermore, one or more members selected from the organic and inorganic substances necessary for the growth of microorganisms or for the production of enzyme may be added to the medium, if necessary.

In the case of solid culture, an appropriate solid medium material, such as wheat bran, is moistened with 0.6 volume of water, autoclaved for 15 minutes at 120° C., inoculated with seed mold, and cultivated for 3 to 5 days. The cultivated wheat bran (Koji) thus obtained is extracted with an appropriate quantity (for example, 6 times its weight) of water at room temperature with gentle stirring for an appropriate time period. The extract is further filtered with diatomaceous earth or centrifuged to give a transparent extract.

In the case of liquid culture, a nutrient medium composed of an appropriate combination of the above-mentioned carbon source, nitrogen source and inorganic salt, for example a medium composed of water, glucose, peptone, ammonium sulfate, yeast extract, $KH_2PO_4$ and the like, is adjusted to pH 5 to 7, sterilized in the same conditions as in the case of solid medium, inoculated with seed mold, and cultivated. Although the cultivation may be carried out by any appropriate culture method such as standing culture, shaking culture, agitation culture, aeration culture, etc., submerged culture with appropriate aeration and agitation is particularly preferable in the case of large-scale cultivation.

Temperature of cultivation may be varied in the range permitting the growth of enzyme-producing mold and the production of enzyme. Preferably, however, the temperature is 20° to 40° C.

Though the time of cultivation varies depending upon the mold used and the type of culture, it is usually in the range of about 1 to 5 days. Advisably, the cultivation is stopped at the time when the accumulated production of enzyme just reaches its maximum.

The culture broth thus obtained in which the enzyme has been produced and accumulated is then subjected to a centrifugation or a filtration with diatomaceous earth to remove insoluble substances including mycelia. The supernatant or the filtrate thus obtained is subjected to salting out using ammonium sulfate or the like to obtain a precipitate, which is dialyzed with a cellulose tubing against an appropriate aqueous solution, and then freeze-dried to give a crude enzyme powder. Otherwise, the supernatant solution or the culture filtrate is subjected to organic solvent precipitation process with alcohol or acetone to give a precipitate, which is then dried in vacuo to give a crude enzyme powder.

In obtaining the enzyme precipitate from the extract agueous solution by means of salting out with ammonium sulfate, it is obtainable at 70 to 80% ammonium sulfate saturation in the case of *Aspergillus japonicus* No. 1744 ATCC 20236, while it is obtainable at 65 to 85% ammonium sulfate saturation in the case of other mold strains. In obtaining the enzyme precipitate by the organic solvent precipitation process, it is obtainable at an alcohol concentration or an acetone concentration of 50 to 70%.

The crude enzyme powder thus obtained is subsequently converted to purified enzyme by various means such as ion-exchange resin chromatography (for example, Amberlite IRC-50), gel filtration on Sephadex (for example, Sephadex G-100, Sephadex G-200 or the like), ion-exchange chromatography on ion-exchange Sephadex (for example, DEAE Sephadex, A-50, QAE Sephadex A50, SE Sephadex or the like). (Sephadex is trademark and manufactured by Pharmacia Fine Chemicals, Sweden, The main structure of said Sephadex is composed of dextran), isoelectric fractionation by the use of Ampholine (Trademark, manufactured by LKB, Sweden), electrophoresis on acetate membrane starch or acrylamide gel, isoelectric precipitation technique, etc. or appropriate combination of these methods.

The novel PE obtainable according to this invention can readily be distinguished from the hitherto known PE by the following procedure. Thus, one makes PE act on a high-methoxyl pectin to produce a low-methoxyl pectin and then fractionates the low-methoxyl pectin obtained by column chromatography on an anion-exchanger such as DEAE-cellulose. In this procedure pectins of higher methoxyl group content are first eluted, which are followed by the elution of pectins of lower methyoxyl content. If pectin concentration in the eluate is successively measured, therefore, it can be easily known whether the pectin molecules are uniform or not with regard to methoxyl group content. Accordingly one can distinguishes the action specificity of the PE employed.

By the above-mentioned DEAE-cellulose chromatography, it can be known that the molecules of the low-methoxyl pectin produced by the novel PE of this invention are almost completely uniform with regard to methoxyl group content. In order to further investigate the distribution of methoxyl group among the pectin molecules, endopolygalacturonase, which is an enzyme capable of randomly hydrolyzing the α-1,4-glycoside bond of pectic acid, was allowed to sufficiently act upon a low-methoxyl pectin having a methoxyl group content of 6.3%, prepared with the novel PE of this invention. Subsequently, after eliminating the methoxyl group from the hydrolyzate a portion of the hydrolyzate was converted to oligomer of galacturonic acid by saponifying it with alkali. The two oligouronide samples thus obtained were fractionated in order of degree galacturonic acid polymerization by means of DEAE-cellulose column chromatography according to the method of Hatanaka et al. [*J. Agric. Chem. Soc. Japan,* 40, 98 (1966)], and degree of polymerization and methoxyl content of the fractions were investigated. As the result, it was found that 90% or more of the low-methoxyl pectin prepared by the novel PE of this invention was degraded into low molecular weight substances comprising 5 or less galacturonic acid units by the action of endopolygalacturonase.

This result indicates that the PE enzyme obtained according to this invention randomly acts upon pectin and randomly hydrolyzes its methoxyl groups.

Next, the means for letting the PE of this invention act upon pectin, namely the means for randomly hydrolyzing the methyl ester bond of pectin with the PE of this invention, may be any of the followings: (1) to pour or spray the PE solution of this invention directly to the plant materials such as peels of fruit before the extraction of pectin therefrom; (2) to add the PE of this invention to the plant materials during the process of extracting pectin from them; and (3) to add the PE of this invention to the pectin extracted from plant materials.

Next, the conditions for the action of the PE of this invention is mentioned as follows. For instance, preferable pH range is 3 to 6 and preferable temperature range is 30° to 50° C. Though the time of the action may be selected appropriately in consideration of the concentration of pectin, the concentration of enzyme and the aimed methoxyl content, it is usually 1 to 10 hours and preferably 1 to 4 hours.

Advisably, the PE of this invention is added to pectin in an amount of 70 to 100 μg in terms of enzyme protein per 1 g of pectin. When the intended reduction of methoxyl group content is obtained said PE is inactivated by a heat-treatment at 70° to 100° C. for about 10 minutes, and the demethoxylated pectin is recovered from the reaction mixture by conventional procedure such as alcohol precipitation or metal salt co-precipitation. According to this invention, demethoxylated pectins having various methoxyl contents can be produced rapidly without occuring any degradation of pectin at all. Further, according to this invention, low-methoxyl pectins having an ability to form strong gel or a pectin having a uniform methoxyl group content, which is decreased so as to satisfy the requirement of the case, can be produced without accessory formation of amide group. Therefore, the process of this invention can be said to be unchallengeably excellent.

The production of various demethoxylated pectin according to this invention will be illustrated by reference to the following experimental example.

Experimental Example

328 Units of PE obtained from a culture of *Aspergillus japonicus* No. 1744 ATCC 20236 was added to one liter of 2% aqueous solution of high-methoxyl pectin (methoxyl content 12.1%), and incubated at 30° C. After 30 minutes, 1 hour, 2 hours and 4 hours, the reaction mixtures were heated at 100° C. for 10 minutes to stop the enzyme reaction, from which pectins having methoxyl contents of 10.5%, 8.5%, 7.5% and 6.3% were prepared, respectively. Calcium chloride was added to each of the pectins obtained, and strength of the resulting gel was measured by means of Curd-meter (Tradename, manufactured by Iio Denki, Japan). The results are summarized in Table 2.

Table 2

| Methoxyl group content (%) | Calcium content (mg/g pectin) | | | | |
|---|---|---|---|---|---|
| | 17.9 | 26.7 | 41.8 | 53.6 | 65.5 |
| | Gel strength ($\times 10^4$ dyne/cm$^2$) | | | | |
| 10.5 | 0 | 2.45 | 4.71 | 6.48 | 6.09 |
| 8.5 | 1.76 | 5.30 | 10.40 | 12.70 | 13.80 |
| 7.5 | 3.14 | 10.60 | 21.30 | 21.20 | 21.20 |
| 6.3 | 5.29 | 21.20 | 33.30 | 30.70 | 25.60 |
| Ammonia method | | | | | |
| 6.1 | 20.6 | 20.80 | 16.60 | 15.60 | 15.10 |

The process of this invention will be illustrated more concretely by reference to the following examples which are given in no limitative way.

EXAMPLE 1

Ninety grams of wheat bran sprayed with 72 ml of top water was cooked in an autoclave at 120° C. for 30 minutes, after cooling it was inoculated with *Aspergillus japonicus* No. 1744 ATCC 20236 and cultivated at 30° C. for 45 hours.

Figure 1:
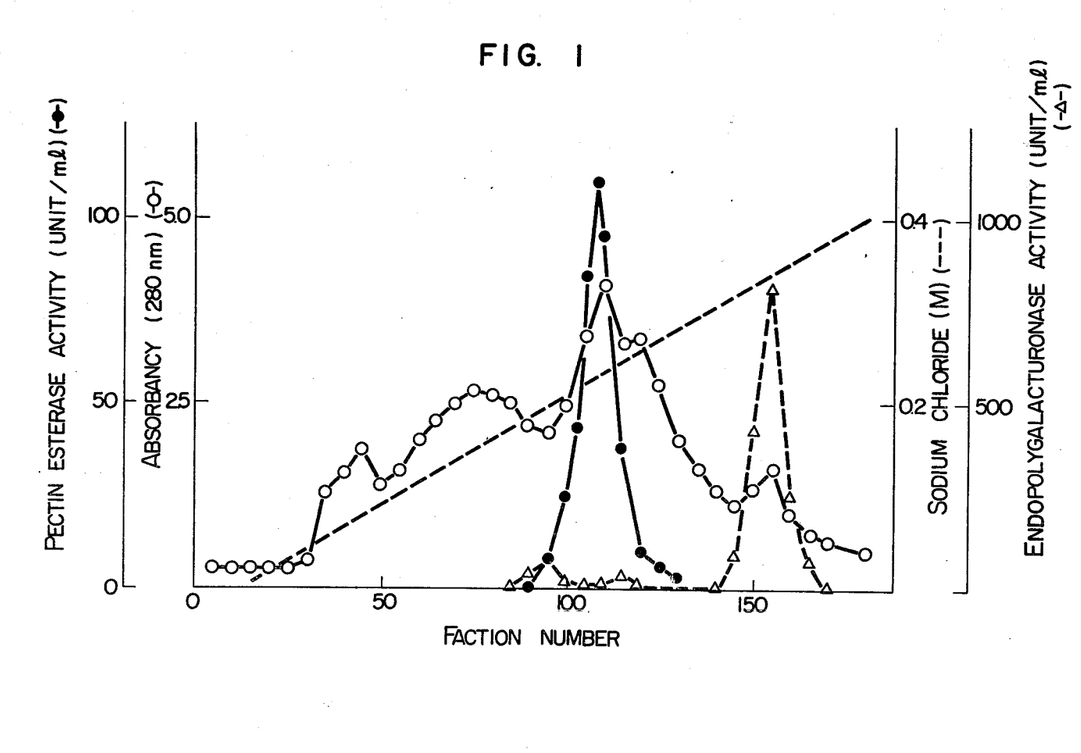
FIG. 1 illustrates the DEAE-Sephadex A-50 column chromatogram of the enzyme of this invention obtained in Example 1.

The Koji thus obtained was mixed with 500 ml of water, stirred gently at room temperature for 2 hours, filtered with a cotton cloth and again filtered with diatomaceous earth. To 400 ml of the extract solution thus obtained, was added 243 g of ammonium sulfate for salting out the enzyme. The precipitated enzyme was collected by centrifugation, dissolved again into 0.1 M acetate buffer solution (pH 5.0), thoroughly dialyzed with a cellulose tubing against the same buffer solution, and then subjected to column chromatography on DEAE-Sephadex A-50. Thus, the dialyzed enzyme solution was let flow down through a column (2φ×35 cm) filled with DEAE-Sephadex A-50 previously equilibrated with 0.1 M acetate buffer solution (pH 5.0) to have the enzyme adsorbed on the column. The column was washed with the same buffer thoroughly, after which the concentration of sodium chloride in the buffer solution was increased for the linear gradient elution of the enzyme. The eluate was divided into 10 ml aliquot fractions. The fractions No. 100 to No. 117 (total volume 180 ml) which had been eluted at sodium chloride concentration between 0.21 and 0.24 M were collected together (cf. FIG. 1 illustrating the column chromatogram of this enzyme on DEAE-Sephadex A-50), dialyzed with a cellulose tubing against distilled water and then freeze-dried.

Figure 2:
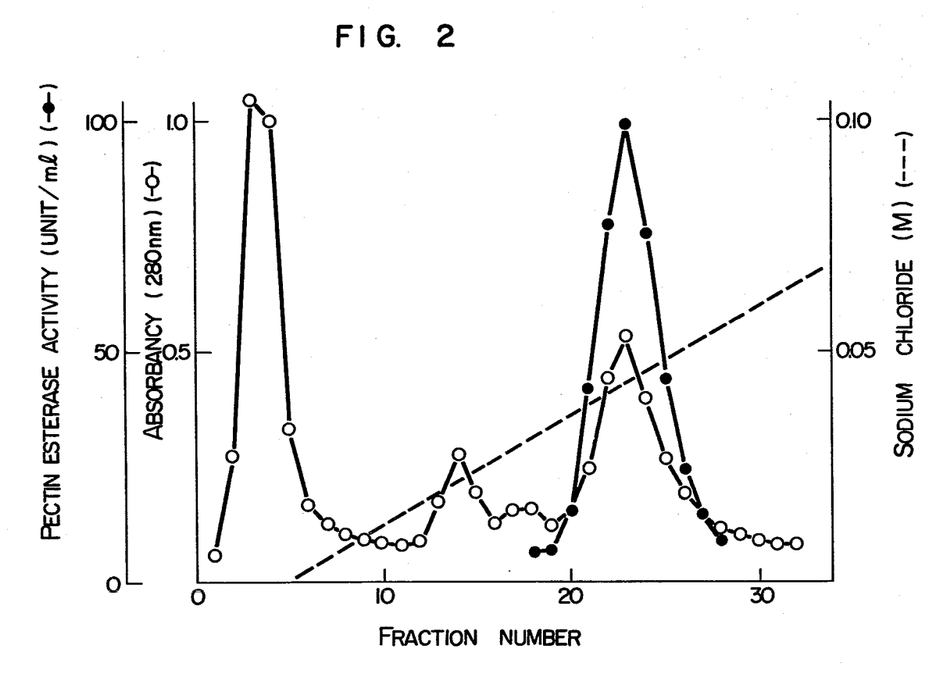
FIG. 2 illustrates the SE-Sephadex column chromatogram of the enzyme of this invention obtained in Example 1.

The dry product was dissolved again into a small quantity of 0.1 M acetate buffer solution (pH 3.8), let flow down through a column (1ϕ×25 cm) of SE-Sephadex previously equilibrated with the same buffer solution (pH 3.8) to have the enzyme adsorbed on the column, and then eluted by means of a linear gradient elution technique with increasing the sodium chloride concentration in the buffer solution. Each aliquot fraction had a volume of 10 ml. The recovered fractions No. 21 to No. 25 (total volume 50 ml) were collected together (cf. FIG. 2 illustrating the column chromatogram of this enzyme on SE-Sephadex), freeze-fried, dissolved again into water, and subjected to gel-filtration through a Sephadex G-100 column (2ϕ×100 cm).

Thus, there was obtained 18.7 mg of a purified enzyme which was not contaminated with any enzyme other than the novel PE of this invention and was recognized to be composed of a homogeneous protein by ultracentrifugation and also by electrophoresis.

Figure 3:
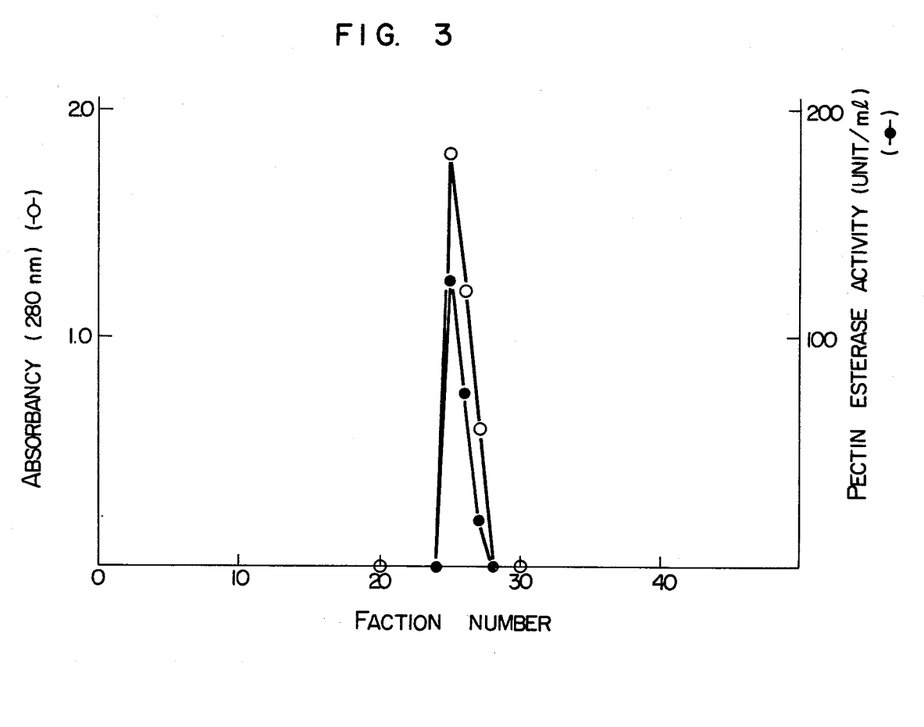
FIG. 3 illustrates the elution pattern of the enzyme of this invention obtained in Example 1 in preparative disk electrophoresis.

FIG. 3 illustrates the elution pattern in preparative disk electrophoresis of the purified enzyme thus obtained.

In another run, the above-mentioned procedures were performed except that *Aspergillus niger* ATCC 1015 was substituted for *Aspergillus japonicus* No. 1744 ATCC 20236. Thus, there was obtained 12.6 mg of a purified enzyme which was not contaminated with any enzyme other than the novel PE of this invention and was also composed of a homogeneous protein as recognized by the both method of ultracentrifugation and electrophoresis.

EXAMPLE 2

In an Erlenmyer flask of 1 liter capacity, 200 ml aliquot of a medium containing 0.1% $NH_4NO_3$, 0.1% $KH_2PO_4$, 0.05% $MgSO_4$ and 1.5% pectin was placed, cooked at 120° C. for 30 minutes, inoculated with *Penicillium chrysogenum* ATCC 10107 and subjected to shaking culture at 25° C. for one week at 140 strokes per minute with a stroke distance of 10 cm. The culture broth obtained was mixed with diatomaceous earth and filtered.

To the filtrate was added three times volume of cold ethanol, and the mixture was left standing overnight at 4° to 5° C. The resulting precipitate was collected by centrifugation and dissolved into 200 ml of 0.1 M acetate buffer solution (pH 5.0). The insoluble matter was removed by centrifugation, and the supernatant was applied to a DEAE-Sephadex column (2×35 cm) previously equilibrated with 0.1 M acetate buffer solution. After the column was thoroughly washed with the same buffer, the enzyme was eluted by means of a linear gradient elution technique with increasing the sodium chloride concentration in the buffer solution. The fractions showing the activity of the novel PE, in the eluate, were collected together and dialyzed with a cellulose tubing against 0.1 M acetate buffer solution (pH 5.0), after which the dialyzed product was again subjected to column chromatography on DEAE-Sephadex under the same conditions as above.

Among the fractions eluted, the fractions showing the activity of the novel PE were dialyzed with a cellulose tubing against 0.1 M acetate buffer solution (pH 4.0) and then applied to a column (1×25 cm) of CM-cellulose previously equilibrated with the same buffer solution as above. The concentration of sodium chloride in the buffer solution was linearly increased for the gradient elution of the enzyme. Among the fractions eluted, the fractions showing the activity of the novel PE were collected together, dialyzed with a cellulose tubing against 0.05 M ammonium acetate buffer solution (pH 5.0) and then freeze-dried. The powder obtained was dissolved again into a small quantity of 0.05 M ammonium acetate buffer solution (pH 5.0), applied to a Sephadex G-100 column (2ϕ×100 cm) previously equilibrated with the same buffer solution, and then subjected to gel-filtration with the same buffer solution.

The fraction thus obtained, having the activity of the novel PE, showed no endopectinase activity and seemed to be homogeneous from the viewpoint of protein chemistry.

Table 3 illustrates the total protein quantity (mg), total activity (units), specific activity (units/mg) and some other values found during the above-mentioned purifying processes, wherein total protein quantity (mg) was measured accoreing to *J. Biol. Chem.*, 193, 265–275 (1951).

Table 3

|  | Volume of solution (ml) | Total protein (mg) | Total activity (units) | Specific activity (units/mg) | Recovery (%) |
|---|---|---|---|---|---|
| Culture filtrate | 1000 | 6800 | 11000 | 1.62 | 100 |
| Fraction precipitated with alcohol | 200 | 2800 | 9900 | 3.54 | 90 |
| Fraction of novel PE in the 1st DEAE-Sephadex chromatography | 150 | 700 | 6000 | 8.57 | 54.5 |
| Fraction of novel PE in the 2nd DEAE-Sephadex chromatography | 100 | 200 | 4400 | 22.00 | 40 |
| Fraction of novel PE in CM-cellulose chromatography | 80 | 70 | 2600 | 37.1 | 23.6 |
| Fraction of novel PE in Sephadex G-100 gel-filtration | 50 | 40 | 1900 | 47.5 | 17.3 |

EXAMPLE 3

Ninety grams of wheat bran sprayed with 81 ml of tap water was sterilized in an autoclave at 120° C. for 30 minutes, inoculated with *Sclerotinia archidis* IFO 5291, and cultivated at 27° C. for 5 days.

To the Koji thus obtained was added 500 ml of tap water, the mixture was stirred at room temperature for 2 hours, and then filtered. The filtrate was mixed with twice volume of cold acetone, and the resulting precipitate was collected by centrifugation and dried under an air stream. 50 g of the crude enzyme thus obtained was dissolved into 500 ml of water, and the insoluble matter was removed by centrifugation. Ammonium sulfate was added to the supernatant up to 0.8 saturation, the resulting precipitate was collected by centrifugation and dissolved again into water, and it was dialyzed with a cellulose tubing against 0.01 M acetate buffer solution (pH 5.5) at 5° C. The inner solution of the dialysis was adjusted to pH 3.0, it was applied to a column of Amberlite IRC-50 (Rohm and Haas Co., U.S.A) previously equilibrated with 0.1 M lactate buffer solution (pH 3.0).

The column was washed with the same buffer solution. After the elimination of the contaminant by eluting off with 0.2 M lactate buffer solution (pH 4.0), the main product was eluted with 500 ml of 0.2 M lactate buffer solution (pH 5.0) and 100 ml of fractions having PE activity were obtained. These fractions were collected together and dialyzed with a cellulose tubing against 0.02 M acetate buffer solution (pH 5.5) and then concentrated to 10 ml in vacuo. The concentrate was adjusted to pH 5.5, it was applied to a column (2φ×35 cm) of DEAE-Sephadex previously equilibrated with 0.02 M acetate buffer solution (pH 5.5), the column was thoroughly washed with the same buffer solution as above, and then the enzyme was eluted by means of a linear gradient elution technique with increasing the concentration of sodium chloride in the buffer solution.

The fractions having the activity of the novel PE of this invention, thus obtained, were collected together and further purified by rechromatography in the same manner as above, and consequently the novel PE of this invention containing no endopectinase was obtained. Table 4 illustrates the total protein quantity, total activity, specific activity and recovery found during the above-mentioned purifying processes.

and the mixture was subjected to shaking culture at 25° C. for 6 days at 140 strokes per minute with a stroke distance of 10 cm. One liter of the culture fluid, thus obtained, was mixed with 20 g of diatomaceous earth and filtered. The filtrate was dialyzed with a cellulose tubing against distilled water at 5° C. for 16 hours and then freeze-dried. The powder thus obtained was dissolved again into a small quantity of water and the insoluble matter was removed by centrifugation. The supernatant was adjusted to pH 6.0 and passed through a DEAE-Sephadex A-25 column (2φ×35 cm) previously equilibrated with 0.1 M acetate buffer solution (pH 5.0). The unadsorbed fractions, namely the fractions having the activity of the novel PE, were collected together and freeze-dried. The powder obtained was dissolved into 2 ml of 0.05 M ammonium acetate buffer solution (pH 5.0), the insoluble material was removed by centrifugation, the supernatant was applied to a column of Sephadex G-75 and eluted with the same buffer solution, and the fractions having the activity of the novel PE of this invention were collected together and freeze-dried.

The dry product was dissolved into a small quantity of 0.05 M acetate buffer solution (pH 5.0) and centrifuged. The supernatant was applied to a column of CM-Sephadex C-50 previously equilibrated with the same buffer solution as above and the column was thoroughly washed with the same buffer solution, after which it was eluted by means of a linear gradient elution technique with increasing the concentration of sodium chloride in the buffer solution. The fractions having the activity of the novel PE of this invention were collected together, freeze-dried, dessolved into a small quantity Table 4

| | Volume of solution (ml) | Total protein (mg) | Total activity (units) | Specific activity (units/mg) | Recovery (%) |
|---|---|---|---|---|---|
| Crude extract solution | 450 | 2500 | 4000 | 1.6 | 100 |
| Fraction precipitated by 0.8 saturation of (NH₄)₂SO₄ | 150 | 800 | 3100 | 3.9 | 77.5 |
| Fraction of novel PE in Amberlite IRC-50 chromatography | 100 | 190 | 2200 | 11.6 | 55.0 |
| Fraction of novel PE in the 1st DEAE-Sephadex chromatography | 80 | 45 | 1400 | 31.1 | 32.5 |
| Fraction of novel PE in the 2nd DEAE-Sephadex chroamtography | 60 | 12.2 | 850 | 70.0 | 21.3 |

EXAMPLE 4

In an Erlenmyer flask of 1 liter capacity, 200 ml of a medium containing 5% of yeast extract (manufactured by Difco Laboratories, U.S.A) and 3% of Pectin N. F. (Trademark, Sunkist Growers, U.S.A) was cooked at 120° C. for 30 minutes, after which it was inoculated with *Fusarium oxysporum* ATCC 15653 and subjected to standing culture at 25° C. for 4 weeks. The culture fluid was removed, 200 ml of the above-mentioned fresh sterilized medium was added to the remaining mycelia, of water, and applied to a column of CM-Cellulose previously equilibrated with 0.05 M acetate buffer solution (pH 3.8). Then it was eluted by means of a linear gradient elution technique with increasing the concentration of sodium chloride in the buffer solution to obtain a novel PE which is free from endopectinase activity.

Table 5 illustrates the total activity, specific activity, and recovery found in the above-mentioned purifying processes.

Table 5

| | Volume of solution (ml) | Total protein (mg) | Total activity (units) | Specific activity (units/mg) | Recovery (%) |
|---|---|---|---|---|---|
| Culture filtrate | 1000 | 250 | 6500 | 26 | 100 |
| Unadsorbed fraction in DEAE-Sephadex A-25 chromatography | 100 | 24 | 2630 | 110 | 40 |

Table 5-continued

| | Volume of solution (ml) | Total protein (mg) | Total activity (units) | Specific activity (units/mg) | Recovery (%) |
|---|---|---|---|---|---|
| Fraction of novel PE in Sephadex G-75 chromatography | 50 | 19 | 2220 | 117 | 34 |
| Fraction of novel PE in CM-Sephadex C-50 chromatography | 100 | 11 | 2050 | 186 | 32 |
| Fraction of novel PE in CM-cellulose chromatography | 40 | 2.4 | 475 | 198 | 7 |

EXAMPLE 5

Into 100 liter of water, 4 kg of a high-methoxyl pectin (methoxyl group content: 12.1%) was dissolved, and to the pectin solution thus obtained, 4100 units of purified PE obtained by the procedure of Example 1 was added. The mixture was incubated at 30° C. for 2 hours, after which the enzyme was inactivated by treating the mixture in a boiling water bath for 10 minutes. An equal volume of ethanol was added to the mixture to precipitate the pectin, and the precipitated pectin was collected by filtration and dried in vacuo. Thus, 3.6 kg of pectin having a methoxyl group content of 10.6% was obtained.

EXAMPLE 6

To 2 kg of high-methoxyl pectin (methoxyl group content: 12.1%), 4100 units of purified PE, obtained by the same procedure as in Example 1, was added, and 1.8 kg of pectin having a methoxyl group content of 6.8% were obtained in the same manner as in Example 1.

EXAMPLE 7

In 30 liters of water, 1 kg of dry peel of Unshu mandarin orange was suspended. After pH of the suspension was adjusted to 2.5 with hydrochloric acid, high-methoxyl pectin was extracted by stirring the suspension at 90° C. for 1 hour. After cooling, the pH of the suspension was adjusted to 4.0 with dilute solution of sodium hydroxide, to which was added 5000 units of purified PE produced by the same procedure as in Example 1. The mixture was incubated at 40° C. for 2 hours, after which the enzyme was inactivated by treating the mixture in a boiling water bath for 10 minutes. It was then filtered with diatomaceous earth to give a transparent filtrate, which was mixed with twice volume of ethanol. The resulting precipitate was recovered and dried in vacuo to give 96 g of low-methoxyl pectin (methoxyl group content 6.3%).

EXAMPLE 8

Into a shaking flask, 50 ml aliquot of a medium containing 1% of wheat bran and 0.5% of pectin was placed, sterilized in an autoclave at 120° C. for 15 minutes, inoculated with *Penicillium chrysogenum* ATCC 10107, and cultivated at 30° C. for 3 days. After cultivation, the mycelia were separated off by centrifugation, and 300 g of ammonium sulfate was added to 500 ml of the supernatant for salting out the enzyme. The precipitate was collected by centrifugation and dissolved again into water. The solution was adjusted to pH 6.5 with 0.1 N-NaOH and allowed to stand at 40° C. for 1 hour. Through this treatment, the contaminative useless enzymes were almost completely inactivated. On the contrary, PE was completely intact.

To 50 ml of a 2% aqulous solution of high-methoxyl pectin (methoxyl group content: 13.6%), 55 units of the PE obtained through the procedure mentioned above was added and incubated at 30° C. for 2 hours. Then, the enzyme was inactivated by treating the mixture in a boiling water bath for 10 minutes, after which 100 ml of ethanol was added to it. The resulting precipitate was collected and dried in vacuo to give 8.8 g of low-methoxyl pectin (methoxyl group content: 6.8%).

EXAMPLE 9

Ninety grams of wheat bran sprayed with 81 ml of tap water was cooked in an autoclave at 120° C. for 30 minutes, inoculated with *Fusarium oxysporum* ATCC 15653 and cultivated at 26° C. for 7 days. To the Koji thus obtained was added 500 ml of water, and the mixture was stirred at room temperature for 2 hours, filtered with a cotton cloth, and again filtered with diatomoceous earth. At room temperature 400 ml of the extract solution thus obtained was stirred for 2 hours together with 1.5 g of DEAE-Sephadex A-50. The DEAE-Sephadex which has adsorbed the enzyme on itself was collected by filtration, from which PE was eluted with 50 ml of 0.5 M sodium chloride solution.

100 units of the PE obtained through the procedure mentioned above was added to 50 ml of a 2% aqueous solution of high-methoxyl pectin (methoxyl group content: 13.6%) and incubated at 30° C. for 4 hours. Then the enzyme was inactivated by treating the mixture in a boiling water bath for 10 minutes, after which 100 ml of ethanol was added to it. The resulting precipitate was recovered and dried in vacuo to give 8.7 g of low-methoxyl pectin (methoxyl group content: 5.3%).

EXAMPLE 10

A mixture consisting of 100 g of wheat bran and 20 g of rice bran was sprayed with 110 ml of tap water and cooked in an autoclave at 120° C. for 30 minutes. It was inoculated with *Sclerotinia libertiana* ATCC 20025 and cultivated at 26° C. for 5 days. To the Koji thus obtained was added 600 ml of water, and the mixture was stirred at room temperature for 2 hours, filtered with a cotton cloth, and then the filtrate was centrifuted. To 500 ml of the supernatant thus obtained was added 266 g of ammonium sulfate for salting out the enzyme, which was collected by centrifugation, dissolved into 0.02 M acetate buffer solution (pH 5.5) and then sufficiently dialyzed with a cellulose tubing against the same buffer solution. The inner solution of the dialysis was passed through a chromatographic column (2×33 cm) of DEAE-Sephadex A-50, from which PE was eluted with 0.02 M acetate buffer solution (pH 5.5) containing 0.2 M sodium chloride.

To 50 ml of a 2% aqueous solution of high-methoxyl pectin (methoxyl group content: 13.6%), 50 units of the PE obtained by the procedure mentioned above was added, and incubated at 30° C. for 1 hour. Then the enzyme was inactivated by treating the mixture in a boiling bath for 10 minutes, after which 100 ml of ethanol was added to it. The resulting precipitate was recovered and dried in vacuo to give 8.5 g of pectin having a methoxyl group content of 9.2%.

What is claimed is:

1. A novel pectin esterase having the following characteristic properties:
    (1) It acts upon the methyl ester bond of pectin to hydrolyze the methyl ester bond randomly; It is specific to the methyl ester bond of pectin and demonstrates no activity on ethyl ester, propyl ester and ethylene glycol ester bonds;
    (2) Its optimum pH for its action is about 4.5 and its stable pH range is 3 to 6;
    (3) Its action temperature is in the range of 25° to 50° C., in particular, 40° to 45° C.;
    (4) It completely loses its activity by heat-treatment at 60° C. for 10 minutes or at a pH value below 2 or above 8;
    (5) It is inhibited by $Hg^{++}$, $Cu^{++}$ and $Ag^+$; There is no particular activator nor stabilizer for it;
    (6) It has a molecular weight of 35,000 as measured at 4° C. in 0.1 M ammonium acetate buffer solution having a pH value of 5.0;
    (7) It is an acidic protein having an isoelectric point of PI 4.1.

2. A process for producing a novel pectin esterase characterized by cultivating, on a medium, a mold strain belonging to Genus Aspergillus, Genus Penicillium, Genus Fusarium or Genus Sclerotinia and having an ability to produce said novel pectin esterase which randomly hydrolyzes the methyl ester bond of pectin, followed by collecting said novel pectin esterase from the culture.

3. A process according to claim 2, wherein said mold strain having an ability to produce the novel pectin esterase is *Aspergillus japonicus* No. 1744 ATCC 20236, *Aspergillus niger* ATCC 1015, *Penicillium chrysogenum* ATCC 10107, *Fusarium oxysporum* ATCC 15653, *Sclerotinia archidis* IFO 5291 or *Sclerotinia libertiana* ATCC 20025.

4. A process according to claim 2, wherein the cultivation is carried out at 20° to 40° C. for 1 to 5 days.

5. A process according to claim 2, wherein said medium contains carbon sources, nitrogen sources and inorganic salts.

6. A process according to claim 2, wherein said medium is a solid medium.

7. A process according to claim 2, wherein said medium is a liquid medium.

8. An enzymic process for the production of demethoxylated pectin characterized by adding, to pectin, an enzyme which randomly hydrolyzes the methyl ester bond of pectin, hydrolyzing the methyl ester bond of pectin therewith, and thereby obtaining a demethoxylated pectin having a uniform methoxy group content.

9. An enzymic process for the production of demethoxylated pectin according to claim 8, wherein said enzyme which randomly hydrolyzes the methyl ester bond of pectin is a culture itself obtainable by cultivating, on a medium, a mold strain belonging to Genus Aspergillus, Genus Penicillium, Genus Fusarium or Genus Sclerotinia and having an ability to produce said enzyme, or a crude enzyme or a purified enzyme obtainable therefrom.

10. A process according to claim 8, wherein the methyl ester bond of pectin is hydrolyzed at a pH value of 3 to 6, at a temperature of 25° to 50° C. for 1 to 10 hours, preferably, 1 to 4 hours.

11. A process according to claim 8, wherein said enzyme is added in an amount of 70 to 100 μg in terms of enzyme protein per 1 g of pectin.

* * * * *